(12) United States Patent
Gerten

(10) Patent No.: US 9,642,526 B2
(45) Date of Patent: May 9, 2017

(54) OPTICAL ARRANGEMENT AND METHOD FOR ASCERTAINING THE ORIENTATION OF AN ARTIFICIAL LENS

(71) Applicant: VOSSAMED GMBH & CO. KG, Cologne (DE)

(72) Inventor: Georg Gerten, Bonn (DE)

(73) Assignee: VOSSAMED GMBH & CO. KG (DE)

( * ) Notice: Subject to any disclaimer, the term of this patent is extended or adjusted under 35 U.S.C. 154(b) by 20 days.

(21) Appl. No.: 14/346,495

(22) PCT Filed: Sep. 20, 2012

(86) PCT No.: PCT/EP2012/003946
§ 371 (c)(1),
(2) Date: Mar. 21, 2014

(87) PCT Pub. No.: WO2013/041230
PCT Pub. Date: Mar. 28, 2013

(65) Prior Publication Data
US 2014/0232986 A1     Aug. 21, 2014

(30) Foreign Application Priority Data
Sep. 23, 2011   (DE) .................. 10 2011 114 251

(51) Int. Cl.
*A61B 3/14*       (2006.01)
*A61B 3/00*       (2006.01)
(Continued)

(52) U.S. Cl.
CPC .................. *A61B 3/14* (2013.01); *A61B 3/10* (2013.01); *A61F 2/1627* (2013.01)

(58) Field of Classification Search
USPC ................................................ 351/206, 246
See application file for complete search history.

(56) References Cited

U.S. PATENT DOCUMENTS

| 4,046,463 A | 9/1977 | La Russa et al. |
| 4,172,639 A | 10/1979 | Lang et al. |

(Continued)

FOREIGN PATENT DOCUMENTS

| CA | 1099965 A2 | 4/1981 |
| CH | 699886 A1 | 5/2010 |

(Continued)

OTHER PUBLICATIONS

PCT International Preliminary Report on Patentability and Written Opinion of the International Searching Authority Translation Dated Apr. 3, 2014, Application No. PCT/EP2012/003946, Applicant VossAmed GmbH & Co. KG., 13 Pages.

(Continued)

*Primary Examiner* — Jack Dinh
(74) *Attorney, Agent, or Firm* — Brooks Kushman P.C.

(57) ABSTRACT

An optical arrangement for ascertaining the orientation of an artificial lens in an eye comprises an observation beam path with an imaging optical system, at least two light-emitting test objects with a defined contour, and one collimation optical system paired with each test object for collimating the light pattern emanating from the test object in a collimation beam path that is directed at the eye. The imaging optical system is designed such that said optical system has multiple observation beam paths with different imaging properties in order to simultaneously image multiple reflected light patterns from different depths of the eye, or the imaging properties of the observation beam paths can be adjusted in a variable manner in order to be able to sharply image sequentially reflected light patterns from different depths.

22 Claims, 6 Drawing Sheets

(51) Int. Cl.
*A61B 3/10* (2006.01)
*A61F 2/16* (2006.01)

(56) References Cited

U.S. PATENT DOCUMENTS

| | | |
|---|---|---|
| 4,572,628 A | 2/1986 | Nohda |
| 4,660,947 A | 4/1987 | Amoils |
| 4,786,163 A | 11/1988 | Imamichi et al. |
| 4,917,458 A | 4/1990 | Matsumura |
| 6,733,129 B2 | 5/2004 | Masaki |
| 7,699,468 B2 | 4/2010 | Gaida |
| 8,708,488 B2 | 4/2014 | Kraus et al. |
| 2002/0154269 A1 | 10/2002 | Liu et al. |
| 2010/0152847 A1 | 6/2010 | Padrick et al. |
| 2011/0122365 A1 | 5/2011 | Kraue et al. |

FOREIGN PATENT DOCUMENTS

| | | |
|---|---|---|
| CN | 1387820 A | 1/2003 |
| CN | 102159128 A | 8/2011 |
| DE | 1547417 A1 | 2/1970 |
| DE | 2643344 A1 | 3/1978 |
| DE | 4316782 C1 | 9/1994 |
| DE | 29517578 U1 | 1/1996 |
| DE | 19817047 A1 | 10/1999 |
| DE | 10017298 A1 | 10/2001 |
| DE | 102005031496 A1 | 1/2007 |
| DE | 102005042436 A1 | 4/2007 |
| DE | 102008034490 A1 | 2/2010 |
| DE | 102009052128 A1 | 4/2011 |
| DE | 102009052135 A1 | 7/2011 |
| GB | 1152973 A | 5/1969 |
| JP | S5134591 A | 3/1976 |
| JP | S54160271 A | 12/1979 |
| JP | S60501992 A | 11/1985 |
| JP | S6318102 U | 2/1988 |
| JP | 01308552 A | 12/1989 |
| JP | 03-114462 A | 5/1991 |
| JP | H0346774 B2 | 7/1991 |
| JP | H0576293 B2 | 10/1993 |
| JP | H0757218 B2 | 6/1995 |
| JP | 2740924 B2 | 4/1998 |
| JP | 4124897 B2 | 7/2008 |
| WO | 2011030509 A1 | 3/2011 |

OTHER PUBLICATIONS

Japanese Office Action Dated Feb. 24, 2015, Application No. JP 2014-531129, 5 Pages.
PCT International Search Report Dated Dec. 10, 2012, Application No. PCT/EP2012/003946, Applicant VossAmed GmbH & Co. KG, 4 Pages.
German Search Report Dated Jul. 24, 2012, Application No. 10 2011 114 251.0, Applicant VossAmed GmbH & Co. KG, 8 Pages.
Japanese Office Action Dated Oct. 13, 2015, Application No. 2014-531129, Applicant Miyoshi, Hidekazu et al., 2 Pages.
Chinese Second Office Action Dated Mar. 23, 2016, Application No. 201280046262.0., Applicant VossAmed GmbH & Co. KG, 10 Pages.
Chinese Office Action Dated Aug. 19, 2015, Application No. 201280046262.0, Applicant VossAmed GmbH & Co. KG, 9 Pages.

OPTICAL ARRANGEMENT AND METHOD FOR ASCERTAINING THE ORIENTATION OF AN ARTIFICIAL LENS

CROSS-REFERENCE TO RELATED APPLICATIONS

This application is a U.S. national phase of PCT Application No. PCT/EP2012/003946 filed Sep. 20, 2012, which claims priority to German Application No. 10 2011 114 251.0 filed Sep. 23, 2011, the disclosures of which are incorporated in their entirety by reference herein.

TECHNICAL FIELD

The invention relates to an optical arrangement and a method for detecting the orientation of an artificial lens in an eye. Such artificial lenses are also referred to as intraocular lenses (IOL). Their orientation, in particular their rotational orientation, is mainly of interest with so-called toric intraocular lenses which have two different radii of curvature in two different main axes and thus two different refractive powers.

BACKGROUND

Surgeries at the human eye lens belong to the surgeries most commonly carried out in the world. Such surgeries become necessary due to pathologic processes which in most cases concern the interior of the eye lens, for example a turbidity of the eye lens (cataract formation) and/or a hardening of the lens core in case of presbyopia. In modern surgery methods, the interior of the eye lens (nucleus, cortex) is removed. For this, the lens capsular bag is preferably only opened from the front and the rest is left as it is. The capsular bag, which is empty after the interior of the natural eye lens has been removed, then generally serves to receive an artificial intraocular lens (IOL) which replaces the removed inner parts of the eye lens and reconstitutes the eyesight of the patient taking into consideration the desired optical correction of the eye.

Modern intraocular lenses may be produced individually for the patient concerned and, for this purpose, have most diverse optical properties with respect to asphericity, multifocality, toric surfaces and the like, to cope with and correct the diverse causes of (natural) ametropia of the patient concerned. For these inherent features of the individually produced lens to perform their function as correctly as possible, a preferably optimal centering of the lens and its association with certain reference systems in the optical system of the eye are strived for. So, the intraocular lens should be in general reliably placed concentrically to the pupil center, taking into consideration the visual line and the center of the entrance pupil, in particular in the capsular bag, but also in the sulcus ciliaris or the anterior chamber of the eye, where especially with toric intraocular lenses or phakic toric IOLs (IOLs which are implanted in addition to one's own lens), an axially accurate positioning is also important. Here, in case of malrotation, the predicted refraction target will deviate from the actually achieved target all the more the greater the rotation and the refractive power of the cylinder portion of the implanted lens are. However, not only the correct orientation in the X- and Y-axis of the optical system of the eye matters, but a preferably permanent and accurate positioning of the lens in the Z-direction (along the optical axis) without any tilting of the IOL is also desired.

While there are measuring and projection systems which may indicate the corresponding refraction and the resulting axes, or via certain reference points the axes in the eye, to the surgeon during surgery, these optical determination systems calculate the power of the IOL from the total refractive power of the eye.

However, a direct measurement of the optical power and position of the lens via their radii of curvature is desirable. Especially if an astigmatism of the eye, which often emanates from the cornea (so-called irregular curvature of the cornea), is to be corrected with an IOL, one has to see that the axis of the corneal astigmatism to be corrected exactly corresponds to the cylinder axis of the toric IOL. Already with a minor malrotation of the IOL axis, major errors in the complete imaging system of the eye are likely to occur; e.g. a malrotation of about 15° of an IOL already results in a loss of 50% of the cylinder correction and a considerable axial rotation of the remaining total error in the optical system.

In toric IOLs, the axis of the cylinder effect is normally indicated by manufacturer' markers on the lens system. These, however, have a certain error tolerance of normally 3° which may lead to corresponding total errors in the refraction of the eye (see above).

Ophtalmologic apparatuses and methods for checking the optical properties of an eye with or without artificial lens are known, for example, from DE 10 2008 034 490 A1, DE 10 2005 042 436 A1, DE 10 2005 031 496 A1, DE 295 17 578 U1, DE 198 17 047 A1, JP 01308552A, CH 699 886 A1, WO 2011/030509 A1, CA 1099965, or DE 26 43 344 A1. It turned out, however, that said apparatuses are either complicate to handle or are not suited for reliably determining the orientation of an artificial lens in an eye.

SUMMARY

The invention is now intended to remedy this situation, and it is the object of the invention to insert an intraocular lens as precisely as possible into the capsular bag, the sulcus ciliaris, or the anterior chamber of an eye and, after it has been correctly orientated in the desired position, to reliably fix this position.

The optical arrangement according to the invention comprises at least two light-emitting test objects with a defined contour. The structured light pattern emanating from these test objects is collimated by a collimation optical system and directed at an eye which is observed via an observation beam path of the optical arrangement by an operator of the optical arrangement, or by a camera, for example. In the patient's eye, multiple optic boundaries exist between the different optical media of the eye. Since indices of refraction change at these boundaries, a retroreflection of the light patterns occurs at the boundaries. Within the scope of the invention, these retroreflections are also referred to as "test targets". Now the heart of the invention consists in being able to retroreflect and compare test targets of known contours and positions of different optical boundaries in the eye simultaneously or sequentially. The most important boundaries are the surface of the cornea and the front and back sides of the implanted artificial lens. Further boundaries would be the back side of the cornea and the retina.

In the invention, the imaging optical system of the observation beam path is configured such that its imaging properties, especially their focusing properties, are adjustable such that the light patterns reflected from different boundaries of the optical media of the eye may be sharply imaged sequentially. The total path by which the focusing of the imaging optical system may be shifted to this end may be, for example, between 0 and 30 mm, preferably about 10 mm. In addition or as an alternative, it would be possible for the imaging optical system to comprise multiple observation beam paths which comprise different imaging properties, in particular different focusing properties. This permits to simultaneously sharply image the light patterns reflected from different depths of the eye to be able to compare them to each other.

One may deduce from the relative position of the light reflections or the test targets from a certain depth of the eye, in particular at the front or back surface of the intraocular lens, the orientation of the lens, in particular the orientation of the main axes in a toric lens. Based on the comparison of the relative positions of the test targets in a certain depth of the eye and the relative positions of the test targets on the surface of the eye, one may moreover determine which rotational orientation relative to an astigmatism of the cornea the intraocular lens has. Here, the quality of the resulting total refractive power or visual acuity of the eye does not necessarily have to be detected. It is rather sufficient that one may deduce, from the relative positions of the light patterns, a rotation (indicating the sense of rotation and the angle of rotation) by which the lens implanted in the eye may be optimally oriented with respect to the astigmatism of the cornea.

The optical arrangement may in particular be designed such that it may be used as apparatus during or after surgery at the human eye, or as laboratory equipment. For example, the optical arrangement could be designed as an optical module and, for an application during surgery, be shifted or folded under a surgical microscope over corresponding mountings or be introduced into the beam path of a surgical microscope. As an alternative, the optical arrangement could, however, also be designed such that it may be used as independent apparatus.

Preferably, the collimation beam paths are each directed onto the eye in a manner non-collinear with the observation beam path, i.e. at an angle to the observation beam path. This leads to a lateral offset of the reflections of the light patterns from different depths or different boundaries of the eye, so that the test targets or the reflections of the light patterns are better detectable.

Angles of 10° to 60°, preferably within a range of 25° to 40°, have proven to be particularly suited angles between the collimation beam path and the observation beam path. With these angle, an easily detectable lateral offset of the test targets is formed while the light emanating from the test objects simultaneously also easily penetrates into deeper regions of the eye.

It is particularly suitable for the angle between the collimation beam path and the observation beam path to be variably adjustable. In this manner, the lateral offset of the test targets in the viewing direction of the observer and the penetration of the light patterns into deeper regions of the eye may be optimized for the respective case of application.

In a suitable variant of the invention, the test objects may be rotated together about an optical axis of the observation beam path. This permits to irradiate test targets from different directions onto the eye even independent of the orientation of the patient's head. From the change of the test targets (i.e. the reflections of the light patterns emanating from the test objects), conclusions may be drawn to the contours of the boundaries between the optical media of the eye, in particular to the position of the main axes of a toric IOL. It would also be conceivable that such conclusions are obtained from the change of a shape of a test target in a rotation of the test objects about the optical axis of the observation beam path, for example from a change of length of a linear test target.

The light-emitting test objects may in principal have any contours. As relatively simple contours, which are nevertheless easily distinguishable, lines, double lines, multiple lines, crosses, hollow crosses, double crosses, multiple crosses, triangles, polygons, arrows, letters, and/or symbols have proven to be suited.

For the test objects to be able to emit light they may be self-luminous, for example as glow wires or as LED arrays. As an alternative, however, the test objects may also be reflective or back-lit, the latter preferably as back-lit slit or gate with a certain contour.

It proved to be advantageous for each test object to differ from another test object by its color and/or contour. This allows the operator of the optical arrangement to quickly associate individual light reflections or test targets in the eye with certain test objects. A distinction of the test objects by colors even permits an unambiguous identification of the individual test targets if these are situated directly one behind the other at a certain observing angle. In addition or as an alternative, the light patterns emanating from the different test objects could also be polarized differently. By means of the different polarizations, test targets that are also situated one behind the other could be resolved, introduced into different observation beam paths by means of polarization-dependent beam splitters, and thus be sharply imaged simultaneously.

The handling of the optical arrangement according to the invention may be further improved by two test objects comprising complementary contours. These may be, for example, two arrows directed towards each other, or a hollow cross (i.e. a non-luminous, cross-shaped field) in connection with a complementary, cross-shaped test target. As soon as during the observation of the eye the two complementary test targets take a certain complementary position, this defines a predetermined orientation with the artificial lens in the eye, for example an orientation of the IOL where the main axes correspond to the main axes of the corneal astigmatism.

In a further suitable variant of the invention, an illumination device with an adjustable light intensity is provided for at least one test object. In general, such an illumination device with adjustable light intensity may be provided for each test object, in particular with an adjustability of the light intensity independent of the light intensity of the illumination devices for other test objects. This permits to compensate differences in the light intensity of the test targets reflected from different depths of the eye. These differences in light intensity may otherwise result from the light pattern having to pass differently long paths in the eye and loosing different amounts of light in the process, in particular by diffusion. The possibility of matching the light intensities of the test targets from different depths considerably facilitates the comparison of the position of the test targets from different depths of the eye.

Further advantageous embodiments of the optical arrangement are conceivable. For instance, a stabilization system against movements of the patient's eye could be additionally provided in the observation beam path, for example according to the multiple image principle. Prisms or similar optical systems could be provided for the image reversion of test targets which undergo lateral reversal in imaging. One or more graduations could be advantageous at an ocular in the observation beam path which indicate, for example, the angles of the collimation beam paths to the observation beam path, certain radii of curvature of the cornea or the IOL, and/or the axial position of an IOL.

The invention also relates to a method for ascertaining the orientation of an artificial lens in an eye. In this method, two or more light patterns which each emanate from a test object with a defined contour and are collimated by means of one collimation optical system each are directed at an eye at angles that are non-collinear with respect to the observation beam path. The light patterns reflected by the front side of the cornea and/or by at least one boundary between the artificial lens and optical media of the eye are sharply imaged simultaneously or sequentially. By changing the rotational angle of the artificial lens in the eye, and/or by changing the angles of rotation of the test objects relative to the eye, the images of the reflections of the light pattern or patterns from the different boundaries of the eye may be optimized, i.e. maximized. With a maximum superimposition of the reflections of the light patterns, an optimal orientation of the artificial lens in the eye is ensured. In a toric IOL, this means that their main axes exactly coincide with the main axes of the cornea astigmatism of the eye.

In a first variant of the method, the imaging properties of the imaging optical system of the observation beam path are modified such that the light patterns reflected by the front side of the cornea and/or by at least one boundary between the artificial lens and optical media of the eye are sharply imaged sequentially. The observer or operator, normally an ophthalmologist, does not have to change his/her own position and the angle of view onto the patient's eye. As an alternative or in addition, multiple observation beam paths with different imaging properties may take care that the reflections of the light patterns from different depths of the eye, for example from the front side of the cornea and/or from at least one boundary between the artificial lens and the optical media of the eye, are sharply imaged simultaneously. This variant has the advantage that the orientation of the artificial lens may be identified even more quickly than in a sequential imaging of the reflections of the light patterns.

The method becomes particularly informative when the angle between the collimation beam path and the observation beam path is changed, and/or when the test objects are rotated together about an optical axis of the observation beam path, so that test targets may be projected from different directions onto the patient's eye.

Further variants of the optical arrangement according to the invention and the method according to the invention are conceivable. They will be described below.

As was already illustrated above, it is conceivable to configure the optical arrangement or the method such that a measurement of the radii of curvature of the artificial eye lens is possible, taking into consideration the position of the test targets reflected by the lens. Thereby, a direct measurement of the power of the lens is also possible without having to perform any calculation for it. In particular, the time-consuming measurement and evaluation of wave fronts may be avoided. The radius of curvature may rather be read out directly from the distance between multiple test targets or from the distance between a test target and the optical axis.

It may be of assistance to couple a light target beam (light pilot beam), for example a laser pilot beam, into the optical arrangement which the patient fixes during examination. Thus, the patient may actively contribute to a position stabilization of his/her eye and thus to an increased precision of measurement. The target beam (pilot beam) may proceed here such that it is positioned centrally to the test targets projected onto the eye. Thereby, an orientation centered to the axis of fixation of the patient's eye is obtained. The coupling of the pilot beam into the optical arrangement may be done at the proximal end of the observation beam path from the position of the patient, or within the observation beam path, for example by means of prismatic components.

It is particularly advantageous for the pilot beam not to be radiated onto the eye in the form of a tiny point, but as an extended object. For example (but not compulsorily), the pilot beam could be projected onto the eye as rotationally symmetric fixation mark, for example as hollow circle, or as a T-shaped marker. By a superimposition of the retroreflections (for example fitting circular light reflections into each other or superimposing T-shaped reflections) from the front surface of the cornea or the front or back surface of the lens, a centering of the intraocular lens onto the fixation axis predetermined by the pilot beam may be obtained.

The examination of the eye is facilitated when a multiple image system (viz. image reduplication system) is arranged in at least one of the observation beam paths. Such a multiple image system is configured to double the image of the eye in an intermediate image plane to thus stabilize the image produced for the observer against movements of the eye.

In this context, it may be advantageous for optical elements, such as prisms or lenses of the multiple image system, to be provided with a coating which is adjusted to the light frequency of the light source used for projecting the test targets onto the eye and onto the artificial lens. The coating could in particular be embodied as narrow-band transmitting filter for the light of the test targets. By this wavelength-sensitive coating, consequently only the light of the test target could be transmitted in an observation beam path, so that double images disturbing the operator are avoided. So, the coating may form a spectrally very narrow filter, so that in the beam path concerned, only the parasitic image of the test target would be seen very brightly, but a double image only very weakly. The coating may be considered as narrow-band filter if it only transmits light within a wavelength range with a FWHM width of about 10 nm without attenuation.

If several such observation beam paths are present, a further improvement offers itself if in at least one of the observation beam paths, a mechanically activated, temporarily usable shutter is provided to be able to temporarily block this observation beam path. By the temporal blocking of one observation beam path, the operator (or surgeon) may switch between a surgery mode without double images and a measuring mode with double images. The shutter may be positioned at any point of one of the observation beam paths.

A multiple image system (image reduplication system) may be embodied to be particularly robust if instead of a multipart lens system, a monolithic design of the multiple image system is obtained by combination of several prisms. In this case, the prisms could also be provided with a coating in the manner described above.

It is furthermore conceivable to rotatably arrange the optical arrangement including the illumination, collimation and observing elements under a binocular microscope such that observation is effected via the one beam path of the binocular microscope, while the second beam path is not influenced and in particular not covered. If by the insertion of the optical arrangement, different optical paths of the two binocular microscope beam paths result, this could be compensated for by suited optical elements, for example prisms.

A further variant would be the introduction of an additional collimation and/or mirror optical system into the observation beam path which is designed to introduce the test targets which are normally reflected to the outside by the curvature of the front surface of the lens again into the observation beam path and make them thus available for measurement. For example, a reflecting ring could be introduced into the observation beam path which reflects the reflections directed outwards again in the direction of the optical axis of the observation beam path, these reflections being made usable for measurement by further optical elements, such as mirrors or prisms.

Below, advantageous embodiments of the optical arrangement according to the invention and the method according to the invention will be illustrated more in detail with reference to a drawing. The figures show in detail:

DETAILED DESCRIPTION

Figure 1:
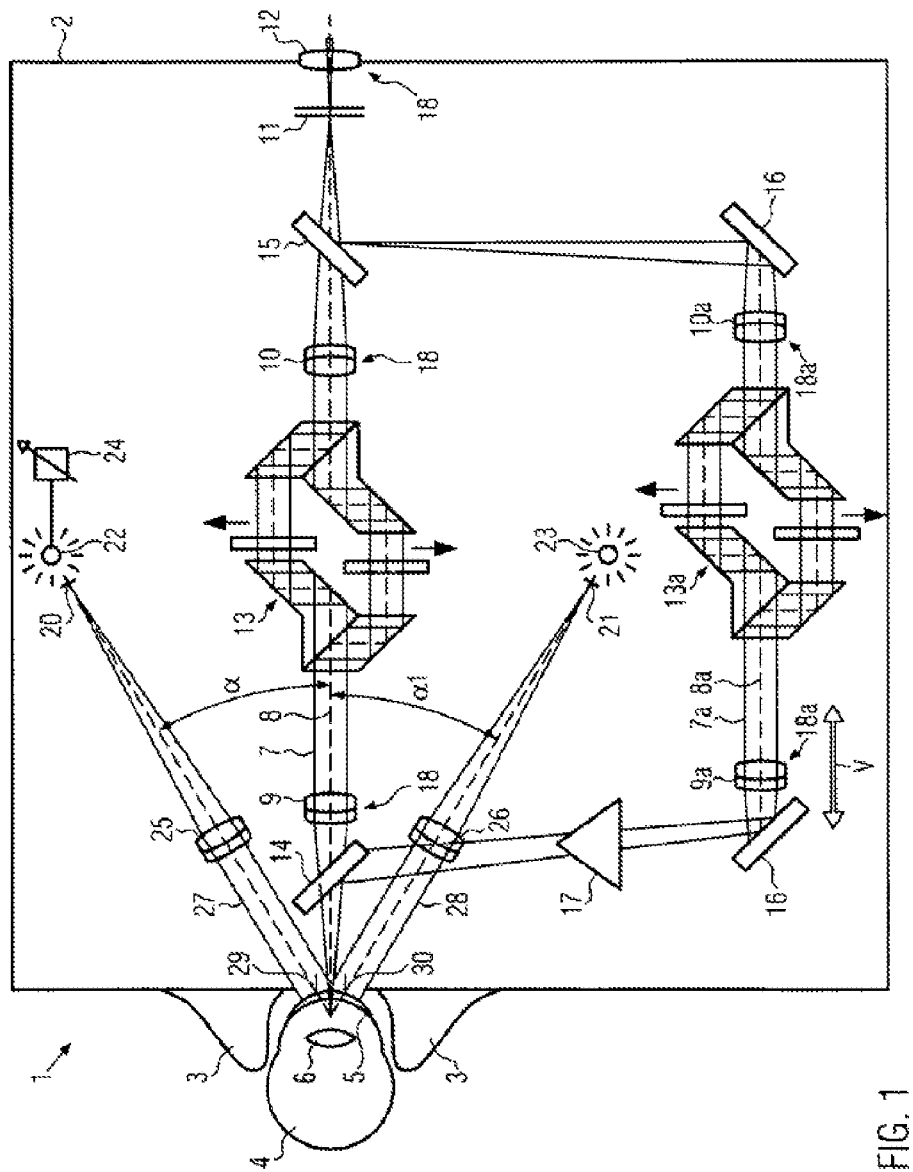
FIG. 1 a schematic representation of an optical arrangement according to the invention, FIG. 2 a representation of the reflections of the irradiated light patterns or the test targets at the eye, FIGS. 3a and 3b some examples of test targets and of the contours of test objects, FIG. 4 a variant of the optical arrangement, FIG. 5 a second variant of an observation beam path, FIG. 6 a third variant of an observation beam path, and FIG. 7 a view of the observation beam path from a patient's perspective.

Similar components are always provided with the same reference numerals in the figures.

FIG. 1 schematically shows an embodiment of an optical arrangement 1 according to the invention. The optical arrangement 1 comprises a housing 2 with which the optical arrangement 1 may be designed as an independent apparatus. As an alternative, it would be conceivable for the housing 2 to be part of a surgical microscope or be introduced into the beam path of a surgical microscope by corresponding mountings, for example by swiveling it into the beam path of the surgical microscope.

At the housing 2, a schematically indicated rest 3 is shown against which a patient may rest his/her head to bring his/her eye 4 into a predetermined position relative to the housing 2 and thus to the optical arrangement 1. The rest 3 moreover assists in keeping the patient's eye 4 in the predetermined position as stably as possible.

The patient's eye 4 is also only schematically shown in FIG. 1. Here, one can see the cornea 5 of the eye, which is oriented to the optical arrangement 1, and the lens 6 of the eye. The lens 6 is in particular an artificial eye lens, also referred to as intraocular lens (IOL).

The optical arrangement 1 has a primary observation beam path 7. The central optical axis 8 of the primary observation beam path 7 defines the direction at which the eye 4 may be observed. In the observation beam path 7, a first objective 9 and a second objective 10 are provided. They serve to generate an image of the observed region of the eye 4 in an image plane 11. By means of an ocular 12 or two oculars 12 arranged one next to the other, this image generated in the image plane 11 is imaged sharply for the viewer. A multiple image system (image reduplication system) 13 is arranged between the two objectives 9, 10. It serves to double the image of the eye 4 in an intermediate image plane to stabilize the image generated for the viewer against movements of the eye 4.

The optical arrangement 1 furthermore includes a second or secondary observation beam path 7a. Via a first beam splitter 14 which is arranged between the eye 4 and the first objective 9, the secondary observation beam path 7a is coupled out of the primary observation beam path 7. Via a second beam splitter 15 which is arranged between the second objective 10 and the image plane 11, the secondary observation beam path 7a is coupled again into the primary observation beam path 7, so that the eye 4 may be observed by the viewer looking through the ocular 12 simultaneously via both observation beam paths 7, 7a. Deflection mirrors 16 direct the secondary observation beam path 7a from its coupling-out of the primary beam path 7 at the first beam splitter 14 to the coupling-in into the primary beam path 7 from the second beam splitter 15.

Just as in the primary beam path 7, in the secondary observation beam path 7a, too, a first objective 9a and a second objective 10a are provided to generate an image of the observed region of the eye 4 and sharply image this image at the ocular 12 for the viewer. Also in analogy to the primary observation beam path 7, an multiple image system (image reduplication system) 13a is also installed in the secondary observation beam path 7a to stabilize the generated image against movements of the eye 4. A difference to the primary observation beam path 7 now consists in that the first objective 9a of the secondary observation beam path 7a is not arranged in a fixed position but may be shifted along the optical axis 8a of the secondary observation beam path 7a. This shifting motion is indicated by a double arrow V. The shifting motion V may be permitted, for example, over a region of up to 10 mm, up to 20 mm, or even up to 30 mm. It permits to sharply image sequentially images from different depths in the eye 4 to the viewer. A further difference to the primary observation beam path 7 consists in that in the secondary observation beam path 7a, image reversion means 17 are provided which are realized by a prism in the present case. They serve to reverse an image which is possibly upside down in the secondary observation beam path 7a.

The two objectives 9, 10 and the ocular 12 together form an imaging optical system 18 of the primary observation beam path 7 which define the imaging properties of this primary observation beam path 7. Analogously, the first objective 9a, the second objective 10a, and again the ocular 12 form the imaging optical system 18a of the second observation beam path 7a and define its imaging properties. By the possibility of shifting the first objective 9a, the imaging properties of the secondary observation beam path 7a are variable or adjustable.

The optical arrangement 1 according to the invention furthermore comprises a first test object 20 and a second test object 21. The two test objects 20, 21 each have a defined, preferably complementary contour. Light is emitted from the test objects 20, 21, in the form of this defined contour. To this end, the test objects 20, 21 may be self-luminous, for example in the form of an LED array or self-luminous foils (OLED). In the represented embodiment, however, the test objects 20, 21 are each gates (holes) provided with the defined contour which are back-lit by an illumination device 22, 23. The illumination devices 22, 23 may here either have the same color, for example in the form of white light, or they could also have different colors for distinguishing the two test objects 20, 21, in particular complementary colors, such as green and red, or different polarizations. In the represented embodiment, the illumination device 22 for the first test object 20 is provided with a control unit 24 by means of which the light intensity 22 of this illumination device 22 may be controlled continuously or gradually.

One separate collimation optical system 25, 26 is associated with each test object 20, 21. Said collimation optical system 25, 26 collimates the contoured light pattern emanating from the respective test object 20, 21, and bundles it into a collimation beam path 27, 28 directed to the eye 4. The light pattern emanating from the test objects 20 and 21 thus reaches the eye 4 as a parallel ray bundle that seems to come from infinity. At the eye, the light is reflected at the boundaries between two optical media with different refractive indices, in particular at the front side or the back side of the cornea 5 and at the front side or the back side of the artificial lens 6, the latter boundary here acting as a hollow mirror. The reflection or the reflected light spot is also referred to as test target 29, 30 within the scope of the invention. These reflections or test targets 29, 30 are sharply imaged for the observer via the two observation beam paths 7, 7a.

The collimation beam paths 27, 28 are located in the optical arrangement 1 each at an angle α, α1 to the optical axis 8 of the primary observing beam path 7. The two angles α, α1 can be the same. In an advantageous embodiment, the position of the test objects 20, 21 and the orientation of the collimation beam paths 27, 28 are variable with respect to the angles α, α1 taken between the collimation beam paths 27, 28 and the observation beam paths 7. A suited mechanism may take care that the angles α, α1 always remain the same. In the proximity of the ocular 12, a graduation may be attached which indicates the respective angles α for the user. As an alternative, this angle could also be superimposed into the ocular 12 with a graduation. Moreover, all test objects 20, 21 are preferably together rotatable about the optical axis 8 of the observation beam path 7 to be able to irradiate the test targets 29, 30 from different directions onto the eye 4.

Figure 2:
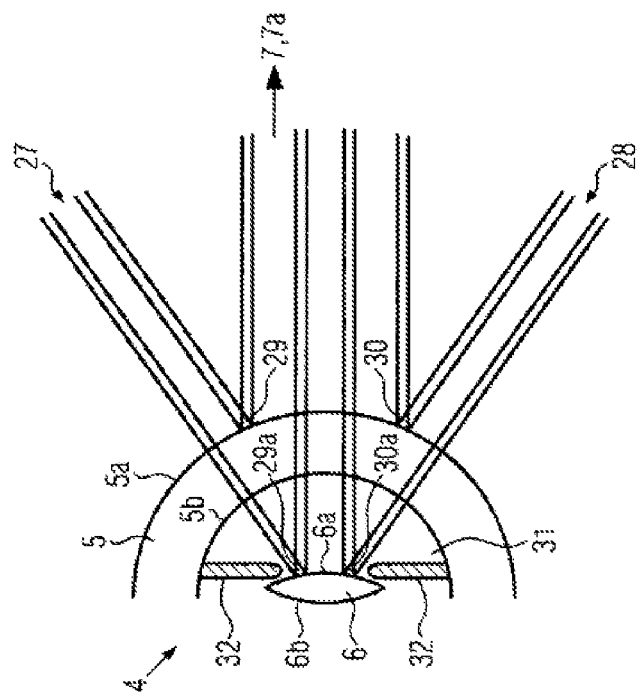

FIG. 2 shows, in an enlarged representation, the situation at the patient's eye 4. Here, only the front media of the eye 4 are represented (not to scale), i.e. the cornea 5, the (artificial) lens 6, and the anterior chamber 31 and the iris 32 situated in-between. At the front side 5a and the back side 5b of the cornea 5 and at the front side 6a and the back side 6b of the lens 6, refractive index steps occur between the different optical media of the eye 4 and between the cornea 5 and air. At these boundaries 5a, 5b, 6a, 6b, due to the refractive index steps, retroreflections of the light patterns of the test objects 20, 21 irradiated via the collimation beam paths 27, 28 occur. One can clearly see in FIG. 2 that the reflections 29, 29a, 30, 30a of these light patterns, which become visible for the viewer via the observation beam paths 7, 7a as bright "test targets", emanate from different depths in the eye. The reflections or test targets 29, 30 here emanate from the front side 5a of the cornea 5, while test targets 29a, 30a emanate from the front side 6a of the artificial lens 6 which are located about 5 to 10 mm underneath the front surface of the cornea 5a. Further reflections or test targets could be reflected from the back side 6b of the artificial lens 6 which there acts as hollow mirror.

Figure 3A:
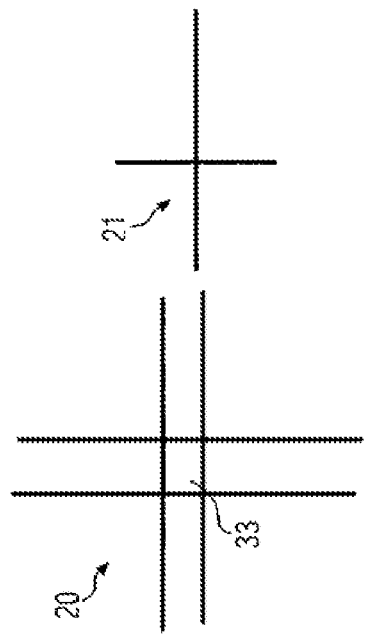

FIG. 3a by way of example shows the contours of two test objects 20, 21 used together. Here, the contour of the first test object 20 consists of a quadruple cross, i.e. of a group of two parallel lines which is cut at right angles by a group of two other, also parallel lines. In the center of the contour of this test object 20, a rectangular, in particular square central region 33 is formed. The contour of the second test object 20 is a simple cross. The contours of the two test objects 20, 21 are insofar complementary with respect to each other that the cruciform contour of the second test object 21 may be oriented such that the centre of this cross is located centrically in the central region 33 of the light pattern of the first test object 20.

Figure 3B:
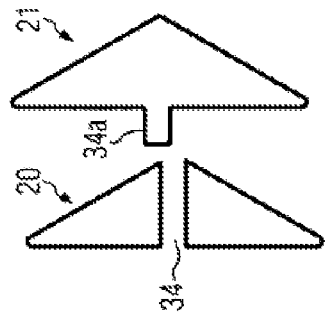

FIG. 3b shows a second embodiment of the contours of the two test targets 20, 21. The first test target 20 shown in the left here has the contour of an isosceles triangle in which a central strip 34 is missing. The second test object 21 has the contour of such an isosceles triangle. Here, however, the central strip is present and even elongated in the form of a projection 34a beyond the triangle. The two test targets 20, 21 are insofar complementary with respect to each other that the elongated projecting section 34a of the second test target 21 may be inserted into the recessed central strip region 34 of the first test target 20.

Below, the operation of the optical arrangement according to the invention and the procedure of the method according to the invention will be described.

First of all, the head of the patient is docked against the optical arrangement 1, in particular by placing the patient's head against the rest 3. This is done after an artificial eye lens 6, optionally a toric eye lens 6, has been inserted into the patient's eye 4. This lens 6 has been manufactured beforehand especially for this patient's eye 4 to compensate defective visions of the eye 4, in particular cornea astigmatism. Manufacturer markers on the artificial lens 6 mark the position of the main axes if it is a toric IOL. These markers are visible for an observer who is looking through the ocular 12 and observes the eye 4 through the observation beam path 7. The markers, however, are not always perfectly aligned with the main axes of the IOL.

This is where the method according to the invention comes into effect. Similar as with a keratometer, the light patterns of a defined contour emanating from the test objects 20, 21 are irradiated onto the eye 4. The reflections of these light patterns are visible for the observer in the form of bright test targets. However, as mentioned above and in particular illustrated with reference to FIG. 2, they emanate from different depths of the eye. To compensate these depth differences, besides the primary observation beam path 7, a secondary observation beam path 7a may now be provided whose imaging optical system 18 generates a sharp image from another depth of the eye 4 than the imaging optical system 18 of the primary observation beam path 7. In this manner, the test targets from different depths of the eye 4 are sharply imaged simultaneously for the viewer. If brightness differences between the test targets exist, and in particular the test targets 29a, 30a reflected from a greater depth in the eye 4 are of lower light intensity than the test targets reflected from higher regions of the eye 4, the brightness differences may be compensated for by controlling the light intensity of the illumination device 22. As an alternative, it is conceivable that in the secondary observation beam path 7a, or in the primary observation beam path 7, mainly if only one observation beam path 7 is present, the imaging properties of the imaging properties of the imaging optical system 18 are variable, in particular by moving an objective 9, 9a. This allows the viewer to sequentially sharply image the test targets that are reflected by the front surface of the cornea 5a or by boundaries in deeper regions of the eye 4 without having to change the viewing angle for this.

In a further step, the viewer may now either change the orientation of the test objects 20, 21 relative to the eye 4, preferably while keeping the distance between the test targets 20, 21 and the eye 4, or he/she may rotate the complete group of all test objects 20, 21 about the optical axis 8 of the primary observation beam path 7. In this manner, the light patterns of the test objects 20, 21 are directed at the eye 4 from different directions. This change of direction in turn permits to superimpose the reflections or test targets caused by the test objects 20, 21. This is facilitated by differences in the contours of the test targets 20, 21 which permit a distinction of the two test targets by the viewer. Maximizing the superimposition of the test targets is even further facilitated by giving the test objects 20 complementary contours as is shown by way of example in FIGS. 3a, 3b. Moreover, the viewer may rotate the artificial lens 6 in the eye 4 if required to maximize the superimposition of the test targets. The viewer recognizes an optimal orientation of the artificial lens 6 in the eye 4 by the superimposition of the light patterns reflected from the front surface of the cornea 5a and from a boundary 6a, 6b of the lens 6 being maximized.

Starting from the represented embodiment, the optical arrangement 1 according to the invention and the method according to the invention may be modified or expanded in many ways. It would be conceivable, for example, to not only provide two test objects 20, 21, but four, six or any other number of test objects 20, 21. It would moreover be conceivable to install cameras with suited image evaluation software into the observation beam paths 7, 7a. In addition to a rotatability about the optical axis 8 of the observation beam path 7, the test objects 20, 21 could also be movable by translation.

By the images of the superimposed or adjacent test targets 29, 30 from different depths in the eye 4 being simultaneously or sequentially brought into a common imaging plane, the retroreflected markers of multiple optical boundaries 5a, 6a, 6b may be compared to each other. This permits e.g. to superimpose the axis of the cylinder portions of the cornea 5 and a toric IOL 6 and to check them for axial concordance. Thereby, a corresponding correction of the rotation or positioning of the IOL 6 may be performed during or after surgery. Here, no calculation of the power of the IOL 6 is performed, but rather a direct measurement of the power and position of the lens 6 via its radii of curvature. Misalignments which could result on the lens 6 due to imperfectly attached manufacturer markers are avoided in the invention. Thereby, the refractive properties of the eye 4 are improved altogether. In contrast to conventional systems which are based on the comparison between images of the patient's eye 4 obtained before and during surgery, moreover errors due to rotational deviations between the images before and during surgery are eliminated in the invention. In the present invention, the position of the IOL 6 and the cornea 5 relative to each other is rather measured independently of a possible rotation of the patient's eye 4 or the complete head of the patient.

Figure 4:
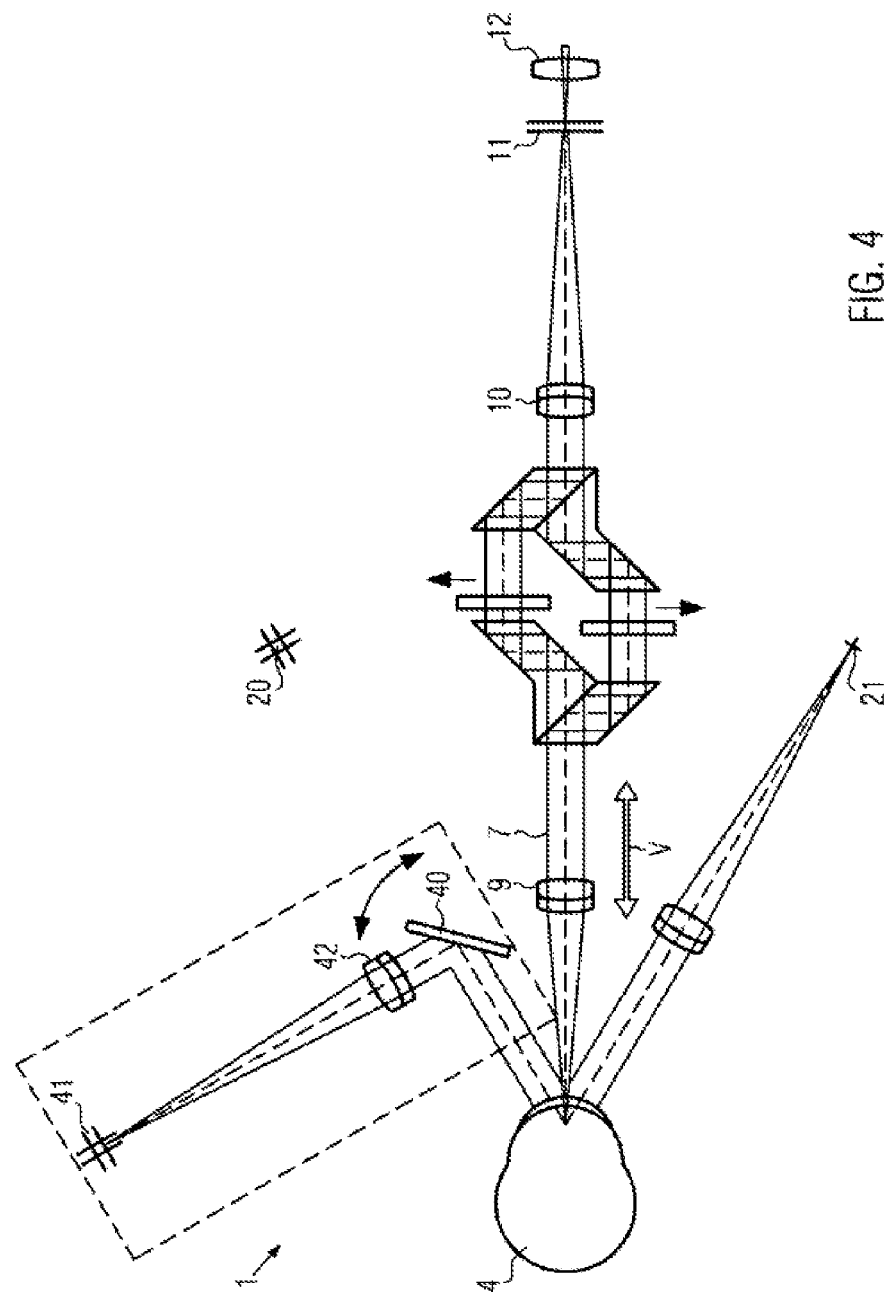

A further variant of the optical arrangement according to the invention 1 with enhanced functionality is shown in FIG. 4. For a better overview, FIG. 4 shows a variant of the optical arrangement 1 with only one single observation beam path 7. To be able to sharply image reflections of the test targets 29, 30 from different depths of the eye 4, the objective 9 may be shifted in this observation beam path 7 as is indicated by the arrow V.

The modification with respect to the first embodiment consists in that the optical arrangement 1 is supplemented by the functionality of a retinoscope. This is done by a swiveling beam splitter or mirror 40 being introduced into the collimation beam path 27 between the first test object 20 and the eye 4. By swiveling this mirror 40 inwards, the collimation beam path is interrupted. Instead, now the light from a slit 41 reaches the eye 4 via a collimation optical system 42. Thereby, a line of light is generated on the eye 4 which may be moved by a movement of the aperture slit 41 perpendicular to the optical axis of the light emitted by it.

The line of light is collimated and moved over the eye 4 to be examined, and the reflection at the retina is viewed through the ocular 12. The direction of the reflection movement during the movement over the region of the pupil is compared to the original moving direction of the slit:

no movement of the reflection: the eye has no ametropia,
following movement: the eye is hyperopic (far-sighted),
movement in opposite direction: the eye is myopic (short-sighted).

The change of the moving directions may also be utilized in case of an astigmatism of the eye 4; for this, the axes with the highest and lowest refractive index may be determined by rotating the line of light and moving it over the pupil. Correspondingly, ametropia may also be determined directly after the implantation of an (astigmatism-correcting toric) artificial lens 6 under the surgical microscope, optionally by comparison before and after the artificial lens has been implanted.

For this, a device is advantageous which couples the line of light to the microscope, so that the reflection may be directly viewed through the ocular 12 of the microscope. The device must be rotatable for determining the axial position, and the line of light must be movable over the pupil of the patient's eye 4 by shifting it in a horizontal direction. To be able to make a comparison of different positions of the rotatable coupling, a marker is attached in the ocular and is adjustable (rotatable).

In this variant of the invention, the optical arrangement 1 comprises a device for rotatably coupling a projection unit consisting of a light source (halogen lamp, LED, . . . ), a slit, a collimation optical system, a beam splitter (altogether as an assembly according to the principle of a retinoscope), and a (horizontal) shifting device, e.g. a ring system connected by a ball bearing underneath or within a surgical microscope. Shifting in the direction of the short slit axis may be achieved e.g. via a threaded device or an electromotive movement. The rotary device is rotatable at least from 0 to 180°, a rotation up to 360 degrees is possible. The shifting region of the line of light on the pupil plane of the patient's eye 4 is 0-25 mm. The slit has a length of 1-25 mm and a width of 0.1-10 mm.

Optionally, at least one of the test targets may be converted to a slit, e.g. by inserting a slit as a projection "shutter" or, with a cross-shaped light source, by reducing the dimension of the image in one direction (retracting a bar of the cross), and fade-in/insert/swivel-in into the beam path of the surgical microscope via a beam splitter in a collinearly movable manner.

Figure 5:
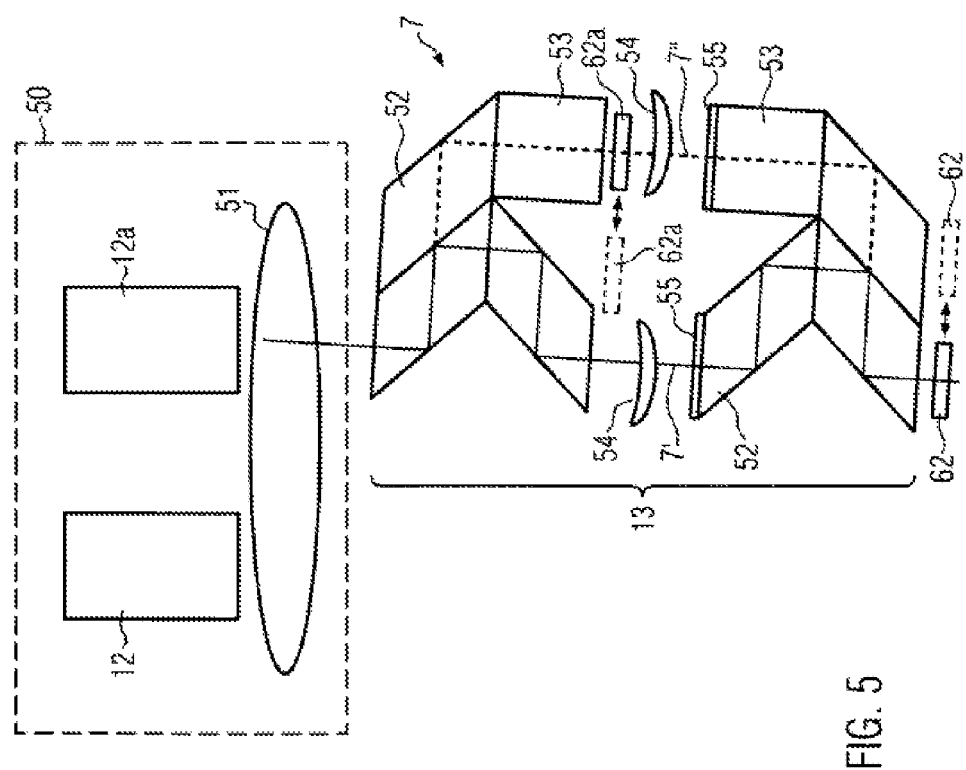

FIG. 5 schematically shows a further variant in which the optical arrangement is coupled to a surgical microscope 50, in particular a binocular microscope. The two oculars 12, 12a of the binocular microscope and a lens which represents the main objective 51 of the surgical microscope are shown. For a better overview, only a part of the observation beam path 7 of the optical arrangement 1 including the multiple image system 13 is shown.

One can see that the multiple image system (image reduplication system) 13 is only arranged in the beam path of the one ocular 12a of the microscope 50, so that the beam path of the other ocular 12 is not influenced. One can furthermore see that the multiple image system 13 comprises a plurality of interconnected prisms 52 and transparent optical blocks 53. These prisms 52 and optical blocks 53 are connected to each other such that a beam splitter arrangement results which divides the observation beam path 7 into two partial beams 7' and 7" and subsequently superimposes these partial beams again. In each of the partial beam paths 7', 7", a free beam path is located in which a lens 54 is placed decentrally. The decentral arrangement of the lenses 54 causes beam deviation.

The optical arrangement including the observation beam path 7 is preferably rotatably coupled to the surgical microscope. It is conceivable to compensate the influence of the multiple image system 13 on the optical path length in the observation beam path of the ocular 12a by a corresponding compensation optical system in the beam path of the other ocular 12, for example using prisms.

It is furthermore conceivable to provide one or several ones of the optical elements 52, 53, 54 of the multiple image system 13 with a coating 55, which is here only by way of example represented on a prism 52 and on a transparent optical block 53. The coating 55 may be a narrow-band transmissive filter for the light emitted by the test objects 20 or the test targets 29, 30.

FIG. 5 furthermore shows by way of example a further feature which may be present in all embodiments of the optical arrangement 1, namely a controllable shutter 62. The latter may be temporarily brought to the position in the observation beam path 7 represented by a solid line to temporarily block this observation beam path 7. Otherwise, the shutter 62 assumes an opened position which is represented by dashed lines.

In addition or as an alternative, a controllable shutter 62a may also be arranged inside a multiple image system 13 such that it blocks only the one partial beam 7" in a position shown by a solid line, while in the opened position (shown by dashed lines) it does not obstruct this partial beam 7". When the shutter 62a is located in the partial beam path 7" and blocks it, double images are prevented because the observer only sees the light which reaches the ocular 12a through the other partial beam path 7'.

Figure 6:
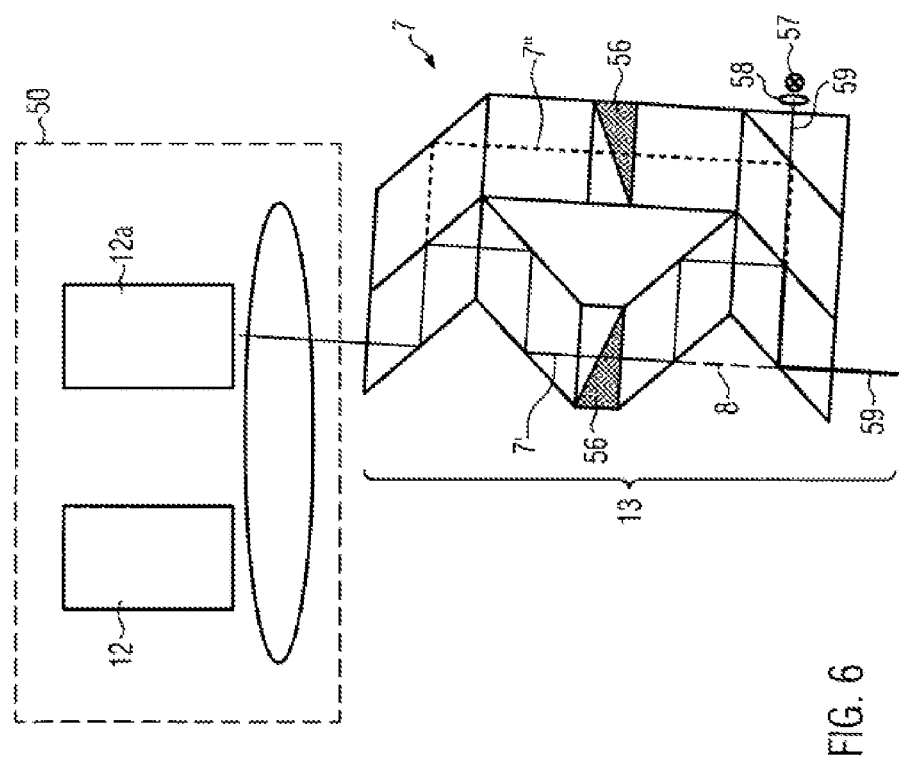

FIG. 6 shows a further modification of the multiple image systems 13 shown in FIGS. 1, 4 and 5. Analogously to FIG. 5, in the situation in FIG. 6, too, the optical arrangement with the represented multiple image system 13 is coupled to a surgical microscope 50, it is in particular only inserted into the beam path of one of the two oculars 12a of the binocular microscope 50. Different to the situation in FIG. 5, the multiple image system (image reduplication system) 13 according to FIG. 6 is now embodied as monolithic system which operates without free beam paths. Instead of the free beam paths with decentralized lenses 54, prism doublets 56 are arranged in each of the partial beam paths 7, 7', 7" which take care of a net beam deviation of the two partial beams.

FIG. 6 also shows a further variation which may be provided in all embodiments of the optical arrangement 1, namely a fixing light (pilot light) 57. The light source for this fixing light 57 may be an LED, a bulb, or a laser. By means of a collimation lens 58, the pilot beam 59 emitted by the fixing light 57 is coupled into the multiple image system 13 and thereby into the observation beam path 7 of the optical arrangement 1. This coupling-in is accomplished such that the pilot beam 59 is directed into the observation beam path 7 parallel to the optical axis 8. During an examination of the eye 4, a patient should and can fix the pilot beam 59 to thus orient his/her eye 4 optimally with respect to the optical axis 8 of the observation beam 7.

Figure 7:
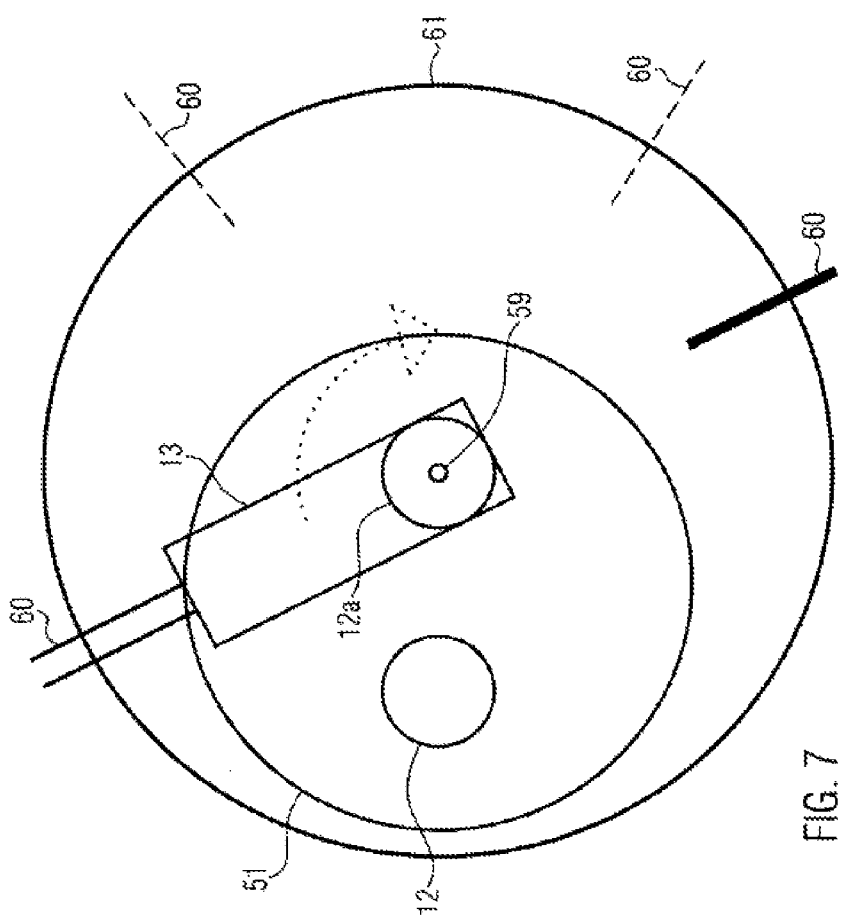

FIG. 7 schematically shows the view of the observation beam path 7 from a patient's view. In the center of the patient's field of view, the pilot beam 59 is located which is to be fixed by the patient. It is located in the center of the region which may be observed through the ocular 12a of the binocular microscope 50. The multiple image system 13 is arranged such that it does not obstruct the observation path of the second ocular 12. Starting from the position shown in FIG. 7, the multiple image system 13 may be rotated in the direction indicated by the dotted arrow by far more than 180°, even by about 270°, without obstructing the observation path of the second ocular 12. At the edge of the field of view, ophthalometer markers 60 and an additional luminous circle 61 may be located which facilitate orientation.

In a further variation, the optical arrangement according to the invention and the method according to the invention could be suited to also measure the axial position of an intraocular lens 6 in the eye, i.e. the position of the lens 6 in the so-called z-axis. This is possible if a known radius of curvature and a known thickness of the intraocular lens 6 are assumed. The measurement of the axial position of the intraocular lens 6 may also be ascertained from the size of the retroreflected test targets or from the distance between different test targets, or from the distance of a test target from the optical axis. With this information on the axial position of the intraocular lens 6, the refractive effect of the lens 6 may be exactly calculated.

The invention claimed is:

1. An optical arrangement for determining orientation of an artificial lens in an eye having a cornea with a front side, the optical arrangement comprising at least one observation beam path with an imaging optical system, at least two light-emitting test objects that each have a defined contour, and one collimation optical system per test object for collimating a light pattern emanatable from the test object into a collimation beam path that is directable at the eye, wherein
    the at least one observation beam path comprises multiple observation beam paths with different imaging properties, which multiple observation beam paths are all directable toward a common ocular and which are adjustable such that light patterns reflectable by different boundary surfaces selected among the front side of the cornea and boundaries between the artificial lens and optical media of the eye are able to be simultaneously imaged.

2. The optical arrangement according to claim 1 wherein each collimation beam path is directable at the eye in a manner non-collinear to any of the observation beam paths.

3. The optical arrangement according to claim 1 wherein an angle between each collimation beam path and a respective one of the observation beam paths is from 10° to 60°.

4. The optical arrangement according to claim 1 wherein the test objects are jointly rotatable about an optical axis of one of the observation beam paths.

5. The optical arrangement according to claim 1 wherein at least one of the test objects is self-luminous, back-lit or reflecting, and/or wherein each test object differs from another test object in its color and/or contour.

6. The optical arrangement according to claim 1 wherein two of the test objects have mutually complementary contours.

7. The optical arrangement according to claim 1 wherein the optical arrangement is configured for measuring radii of curvature of the artificial lens.

8. The optical arrangement according to claim 1 wherein a pilot beam is coupled into the optical arrangement to be fixated by a patient.

9. The optical arrangement according to claim 1 further comprising an image reduplication system arranged in one of the observation beam paths.

10. The optical arrangement according to claim 9 wherein the image reduplication system includes an optical element that is provided with a coating which is embodied as transmissive filter for light that is emanatable from the test objects.

11. The optical arrangement according to claim 9 wherein in at least one of the observation beam paths and/or in a partial beam path of the image reduplication system, a controllable shutter is provided.

12. The optical arrangement according to claim 9 wherein the image reduplication system is designed monolithically by combination of multiple prisms.

13. The optical arrangement according to claim 1 wherein the optical arrangement is rotatably mountable to a binocular microscope.

14. A method for determining orientation of an artificial lens in an eye having a cornea with a front side, the method comprising:
    observing the eye via at least one observation beam path;
    irradiating light patterns, which emanate from at least two test objects and are collimated by one collimation optical system per test object, onto the eye at angles that are non-collinear with the at least one observation beam path, wherein each of the test objects has a defined contour;
    simultaneous or sequential imaging of light patterns reflected by several boundary surfaces selected among the front side of the cornea and boundary surfaces between the artificial lens and optical media of the eye;
    changing a rotational angle of the artificial lens in the eye and/or angles of rotation of the test objects about an optical axis of one of the at least one observation beam path for maximizing a superimposition of an image of reflections of the light patterns from the selected boundary surfaces.

15. The method according to claim 14 wherein the at least one observation beam path includes an imaging optical system, and imaging properties of the imaging optical system are changed such that the light patterns reflected by the selected boundary surfaces are imaged sequentially.

16. The according to claim 14 wherein by means of multiple observation beam paths with different imaging properties, the reflections of the light patterns from the selected boundary surfaces are imaged simultaneously.

17. The method according to claim 14 wherein a pilot beam to be fixated by a patient is coupled into an optical arrangement for carrying out the method.

18. The method according to claim 14 wherein by means of an image reduplication system arranged in at least one observation beam path, a stabilization of an image generated for a viewer against movements of the eye is accomplished.

19. The method according to claim 14 wherein one of the at least one observation beam path and/or a partial beam path are/is temporarily blocked in an image reduplication system by a controllable shutter.

20. The method according to claim 14 wherein a centering of the lens is checked via a central-symmetrical arrangement of retroreflections of the selected boundary surfaces.

21. The method according to claim 14 wherein by means of size measurement and/or size comparison of the reflected light patterns of the selected boundary surfaces, a determination of position of the lens in an axial direction along an optical axis is effected.

22. An optical arrangement for determining orientation of an artificial lens in an eye having a cornea with a front side, the optical arrangement comprising:
    a single observation beam path with an imaging optical system, the observation beam path being adjustable in its imaging properties such that light patterns reflectable by different boundary surfaces selected among the front side of the cornea and boundaries between the artificial lens and optical media of the eye are able to be imaged sequentially;
    at least two light-emitting test objects that each have a defined contour; and
    one collimation optical system per test object for collimating a light pattern emanatable from the test object into a collimation beam path that is directable at the eye.

* * * * *

UNITED STATES PATENT AND TRADEMARK OFFICE
CERTIFICATE OF CORRECTION

PATENT NO. : 9,642,526 B2
APPLICATION NO. : 14/346495
DATED : May 9, 2017
INVENTOR(S) : Georg Gerten et al.

Page 1 of 1

It is certified that error appears in the above-identified patent and that said Letters Patent is hereby corrected as shown below:

In the Claims

Column 15, Line 36, Claim 16:
After "The" and
Before "according"
Insert -- method --.

Signed and Sealed this
Fifteenth Day of August, 2017

Joseph Matal
*Performing the Functions and Duties of the
Under Secretary of Commerce for Intellectual Property and
Director of the United States Patent and Trademark Office*